United States Patent [19]
Jackson, III

[11] Patent Number: 6,047,201
[45] Date of Patent: Apr. 4, 2000

[54] INFANT BLOOD OXYGEN MONITOR AND SIDS WARNING DEVICE

[76] Inventor: William H. Jackson, III, P.O. Box 4795, Wilmington, N.C. 28406

[21] Appl. No.: 09/054,033

[22] Filed: Apr. 2, 1998

[51] Int. Cl.[7] .................................................. A61B 5/00
[52] U.S. Cl. ........................... 600/344; 600/323; 128/903
[58] Field of Search .................................. 600/323, 338, 600/340, 344; 128/903

[56] References Cited

U.S. PATENT DOCUMENTS

| | | |
|---|---|---|
| 4,765,340 | 8/1988 | Sakai et al. . |
| 4,869,253 | 9/1989 | Craig, Jr. et al. . |
| 4,889,116 | 12/1989 | Taube . |
| 5,251,632 | 10/1993 | Delpy . |
| 5,273,036 | 12/1993 | Kronberg et al. . |
| 5,329,931 | 7/1994 | Clauson et al. . |
| 5,490,523 | 2/1996 | Isaacson et al. . |
| 5,505,199 | 4/1996 | Kim . |
| 5,549,113 | 8/1996 | Halleck et al. ............... 128/903 |
| 5,575,284 | 11/1996 | Athan et al. ................. 600/323 |
| 5,586,552 | 12/1996 | Sakai . |

OTHER PUBLICATIONS

Four pages from a Palco Labs Catalog;.
Two pages from a Nonin Medical Inc. Catalog;.
Two pages from a Burdick Pulse Oximeter Catalog;.
Two pages from a Medical System International Corp. Catalog;.
Two pages from a Healthdyne Technologies Catalog.

*Primary Examiner*—Eric F. Winakur
*Attorney, Agent, or Firm*—Michael E. Mauney

[57] ABSTRACT

A device to help a caregiver monitor an infant to discover the onset of a Sudden Infant Death Syndrome event and to intervene to prevent the Sudden Infant Death Syndrome event. A foot and ankle wrap containing rechargeable batteries and a radio transmitter is connected to a toe cap containing a pulse oximeter by adjustable cords. Blood oxygen and pulse readouts from the pulse oximeter are transmitted to a monitor kept by the caregiver. Visible readouts of the blood oxygen and pulse are shown on the monitor for continuous view by the caregiver. The monitor sounds an alarm if the infant's blood oxygen drops to a dangerous level for predetermined period. The time delay prevents false alarms, therefore, provides a greater degree of alertness to the caregiver using the device. When not in use the device is recharged on a stand.

18 Claims, 7 Drawing Sheets

INFANT BLOOD OXYGEN MONITOR AND SIDS WARNING DEVICE

BACKGROUND OF THE INVENTION

1. Field of Invention

This invention is a monitoring device to detect warning signs indicative in Sudden Infant Death Syndrome (SIDS) and other respiratory or cardiac conditions threatening to infants. It is designed to minimize false alarms, to be easily used by parents or other caregivers who have no special training, to be portable, affordable, and practical.

2. Description of Related Art

Sudden Infant Death Syndrome is the term used to designate the death of seemingly healthy infants commonly between the ages of two weeks and one year. Sudden Infant Death Syndrome [usually abbreviated SIDS, sometimes called crib death] is the leading cause of infant deaths up to the age of one year.

The exact cause of SIDS has not been determined. It has been suggested that SIDS occurs in healthy infants as the result of the occurrence of a series of unrelated events. Infants who have periods of apnea, changes in skin color, changes in muscle tone, or who sometimes require help in breathing are more likely to die of SIDS. It is sometimes thought that the infant's position in the crib is a factor in SIDS, and various arrangements of pillows around the infant have been proposed to reduce the risk of SIDS.

A number of systems have been proposed to alert a parent or other caregiver of physiological changes that may be characteristic of the beginning of a SIDS episode in infants. It is believed if parents have warning of respiratory distress, they can intervene before an episode becomes irreversible. For example, alarm systems have been designed to detect if an infant has stopped breathing or if the infant's heart rate has slowed significantly. These apnea/bradycardia alarm systems have been available for home use since the late 1970's. These alarm systems use electrodes attached to the infant's skin. They provide an audible alarm if the infant stops breathing for a predetermined period or if the heart rate drops below a designated level. However, these instruments require electrodes attached to the infant's skin that are connected to the monitor by wires. The wires can be hazardous to an infant. Further, these types of monitoring systems are subject to false alarms. Many false alarms can lead to reduced watchfulness by the caregivers. Moreover, each false alarm can be a cause of parental anxiety. For a monitoring system to be practical and successful, false alarms must be minimized.

A different technology has been employed to monitor for the beginning of a SIDS episode. This technology uses a pulse oximeter, which monitors the pulse rate and the oxygen saturation in the blood. It is thought that a drop in the oxygen saturation to an unsafe level (hypoxemia) is the first event to occur in the SIDS. As such, the pulse oximeter is a means of monitoring hypoxemia, hence it can give early warning of a SIDS episode. Pulse oximeters operate by measuring a light signal passed through an extremity. This light signal changes, depending on the oxygen saturation of the red blood cells. These probes are typically placed on a finger, toe, hand, or foot of the infant being monitored. Placement on the extremities, however, makes the probe susceptible to motion artifacts. By positioning the $O_2$ saturation probe on the infant's sternum or back, the motion of the probe, therefore, false alarms may be reduced. However, again, the wires connecting these probes to the central monitoring unit have drawbacks.

One system has been proposed that uses a combination of pulse oximeter, motion detector, and video camera (see Kim, U.S. Pat. No. 5,505,199). This proposes a motion sensor, video camera and pulse oximeter all be placed in the infant's room and connected to a central unit in the monitoring room, usually the parent's room. The Kim '199 patent states claims that the use of a motion detector with a pulse oximeter and with a video monitor is successful in reducing the number of false alarms. However, it requires a video camera and a motion detector and a pulse oximeter all connected to a video monitor. This requires extensive wiring and instrumentation and is prohibitively expensive for most parents. Additionally, it presumes the monitoring will only occur from the location of the central monitoring unit, including the video display. This means that the caregiver must be close to the central monitoring unit while the device is in use. Also the infant must be sleeping in the room equipped with the camera, motion detector, and oximeter.

Pulse oximeters typically use a sensor attached to a finger or other extremity. This sensor is conductively coupled to an electronic device that measures and provides a readout of the percentage of oxygen in arterial blood. For example, the Isaacson et al., U.S. Pat. No. 5,490,523 discloses a pulse oximeter with a miniature measuring readout device attached and incorporating the sensor. The Isaacson design eliminates the conductive cables that connect the sensor to the readout. Isaacson claims the conductive cables can become damaged during use. His design eliminates the connecting cable, hence, eliminates the problem of cable connection failure. The Isaacson et al. patent shows an extremely small, lightweight and durable pulse oximeter that is battery operated.

Many parents or other caregivers utilize a battery-powered, sound-receiving and broadcast unit, often called a baby monitor. The broadcast unit incorporates a microphone with a compact radio transmitter powered by a battery. This is placed by the crib or other sleeping site of an infant. Should the infant wake and begin to cry or make other unusual noises, the sound created by the infant will be received by the microphone and converted to a low-power radio signal, which is broadcast to a portable receiving unit. This receiving unit is also compact, battery-powered, and contains a receiver and speaker to convert the radio signal back into a sound wave. The receiving unit is carries from room to room so if the baby begins to cry, even if in a remote part of the house, the caregiver will hear the cry through the receiving unit, which is kept with him as he moves from room to room in the house. This device will readily allow a parent to intervene in the event the infant is crying. However, SIDS, by its very nature, is a silent event and difficult to detect by monitoring the infant's sounds alone.

It is believed that none of the above described devices provides an effective way for parents to monitor an infant for the beginning of a SIDS event in time to allow the parent or other caregiver to intervene before the event becomes irreversible. For a device to be effective, it should be affordable for parents or other caregivers of even modest means. Second, it should be easily operated and should not require special training. Third, it should be easily attached to the infant and comfortably worn as to not interfere with the normal sleep of the infant. Fourth, it should not require connecting cables or cords in which the infant could get tangled. These cables or cords are subject to failure over time and can pose a danger to an active infant. Fifth, the device should be resistant to false alarms from motion artifacts or other causes. Sixth, it should be portable so that a parent or other caregiver is not tied to a particular room to monitor the SIDS alarm, nor is the infant required to sleep in a particular room. Therefore, both the unit placed on the infant and the unit giving the alarm should both be portable and lightweight.

SUMMARY OF THE PRESENT INVENTION

The present invention has two main parts. First is a compact battery-powered pulse oximeter generally of a type like that described in the Isaacson et al. U.S. Pat. No. 5,490,523. However, the pulse oximeter, instead of having a calculating unit and readout to give blood oxygen results, has a small transmitting unit, most likely using low power radio waves, to communicate the data gathered by the pulse oximeter to a remote monitoring and read-out unit. This pulse oximeter will be attached to an infant's extremity, preferably the foot, by means of a miniature hook-and-eye attaching means called by the trade name VELCRO™. A cap will slide over a toe, which will contain the actual pulse oximeter sensing unit. No cable connections from the sensor to a monitoring and readout unit are necessary. Once attached to an infant it may be left in place during the duration of the infant's sleep period. This unit will be battery-powered and will have means to advise users of low battery power or in the event the device stops functioning.

The second part is a remote monitoring and readout unit. This unit is compact and battery-powered so that it can be carried by the caregiver. It will receive signals from the pulse oximeter to provide monitoring of the infant's blood oxygen and pulse. There will be a dedicated central processing unit to translate and process the signals from the pulse oximeter. If the blood oxygen drops below a predetermined level for a predetermined period of time, then the monitor unit will give an alarm. A time delay will guard against false alarms generated by motion artifacts and the like. The monitor will also give an alarm in the event it is not receiving signals from the remote sensing unit or in the event that battery power is low.

Both the pulse oximeter and monitoring units are easily constructed of readily available technology. It is believed they can be affordable and durably constructed and will be easily operated requiring no special expertise in training to apply and to use. The units will allow the baby to be placed in any room convenient for the baby's sleeping and will allow the caregiver to monitor the baby's condition continuously from any place within range of the transmitting radio signal from the sensing unit. The unit will give an alarm in the event a predetermined level of low blood oxygen is detected for a predetermined period of time, allowing the caregiver to intervene immediately to determine the cause of the low readings.

DETAILED DESCRIPTION OF THE DRAWINGS

The infant blood oxygen monitor and SIDS warning device (1) has two operative parts. First is a foot sensing unit (5) shown in FIG. 1 and FIG. 2. Second is a monitoring unit (70) shown in FIG. 4 and 4A. First, consider FIG. 1. The foot sensing unit (5) of the current invention is shown attached to an infant's foot. The foot sensing unit (5) consists of two connected pieces. First is a wrap unit (6). The wrap unit (6) is attached to and around an infant's foot. An ankle wrap portion (7) of the wrap unit (6) wraps around the ankle of the infant. An arch wrap portion (8) of the wrap unit (6) wraps around the arch of an infant's foot. The ankle wrap portion (7) and the arch wrap portion (8) are connected by the connecting portion (9). There is a transmitting unit (20) mounted within the arch wrap portion (8) so that when attached to an infant's foot the transmitting unit (20) will be on top of the infant's foot opposite from the arch of the infant's foot. The second piece of the foot sensing unit (5) is a toe cap pulse oximeter (30) which is attached to the arch wrap portion (8) of the wrap unit (6) by an elastically mounted connecting wires (21) and an elastic connecting piece (22). In the same general location as the transmitting unit (20) is a power source (25) for powering both the transmitting unit (20) and the toe cap oximeter (30). Its part of the power source (25) there is a low-voltage sensor connected to a warning light (23). This is to advise users in the event that the power source (25) is becoming depleted. For most applications, the power source (25) will be batteries of a conventional design. Replaceable mercury or longer lasting replaceable lithium batteries can be used. However, the preferred power source (25) is a rechargeable nickel cadmium battery. If rechargeable nickel cadmium batteries are used as the power source (25), a charging inlet (24) will be in proximity to the power source (25). The toe cap oximeter (30) contains a light emitting unit (35) and a light sensing unit (40). Light is emitted by the light emitting unit (35) and passes through the toe of the infant to be received by the light sensing unit (40). Signals generated by the light sensing unit (40) pass through the connecting wires (21) to the transmitting unit (20) for broadcast to the monitoring unit (70) (not shown in FIG. 1). The connecting wires (21) contains means for transmitting power from the power source (25) to the toe cap oximeter (30) as well as means for transmitting signals generated by the light sensing unit (40) to the transmitting unit (20). The wrap unit (16) is attached to the infant's foot by miniature hook and eye connecting means (41) shown in more detail in FIG. 2.

Figure 1:
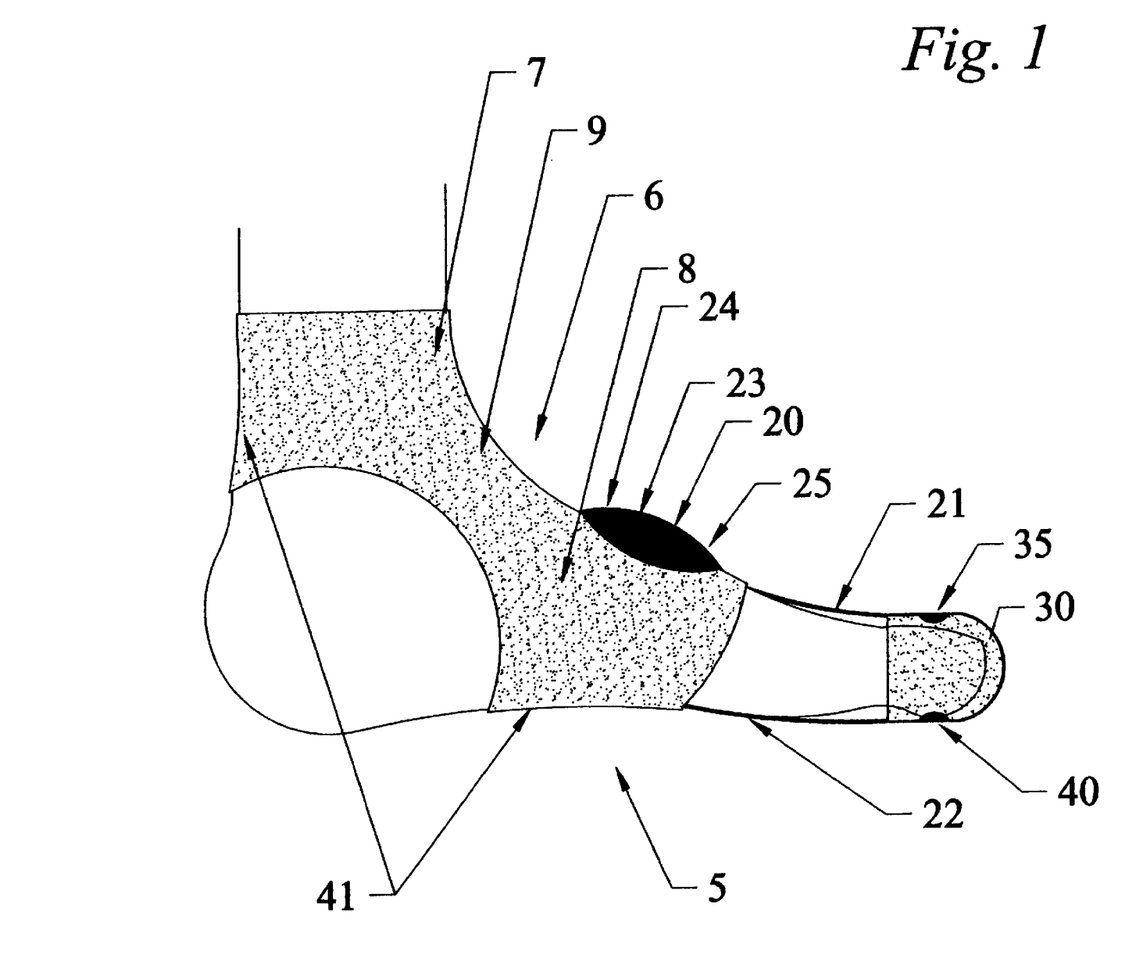
FIG. 1 shows the foot sensing unit of the current invention seen from the side.

The general construction and functioning of pulse oximeters are well known to those of skill in the art. A pulse oximeter ordinarily is applied to some extremity of the patient. It can be a finger, a toe, the bridge of the nose, the ear, or in an infant across the lateral aspect of the foot. A number of manufacturers make a variety of pulse oximeters that operate basically the same way although they may differ in details. Among these manufacturers are Palco Labs, Medical Systems International Corporation, Promedix Corporation, among many others. Typically, these operate by use of a light emitting diode (LED) to emit light at different frequencies or colors. This light passes through the portion of the body of which the pulse oximeter is placed. A light sensor is placed to receive the light after it has passed through the body of the patient to which the sensor is applied. Commonly, the sensor is immediately opposite from the light emitting diodes, as is shown in FIG. 1. However, it may be adjacent to the light emitting diode in reflective pulse oximeters where a reflecting piece is placed opposite from the light emitting diodes so that the light first passes through the patient, is reflected by the reflective piece, passes back through the patient to be received by the sensor. Pediatric models are available that fit on the great toe of an infant. In FIG. 1 the pulse oximeter is shown as a toe cap (30) However, different locations are feasible and could be used under different circumstances.

Figure 2:
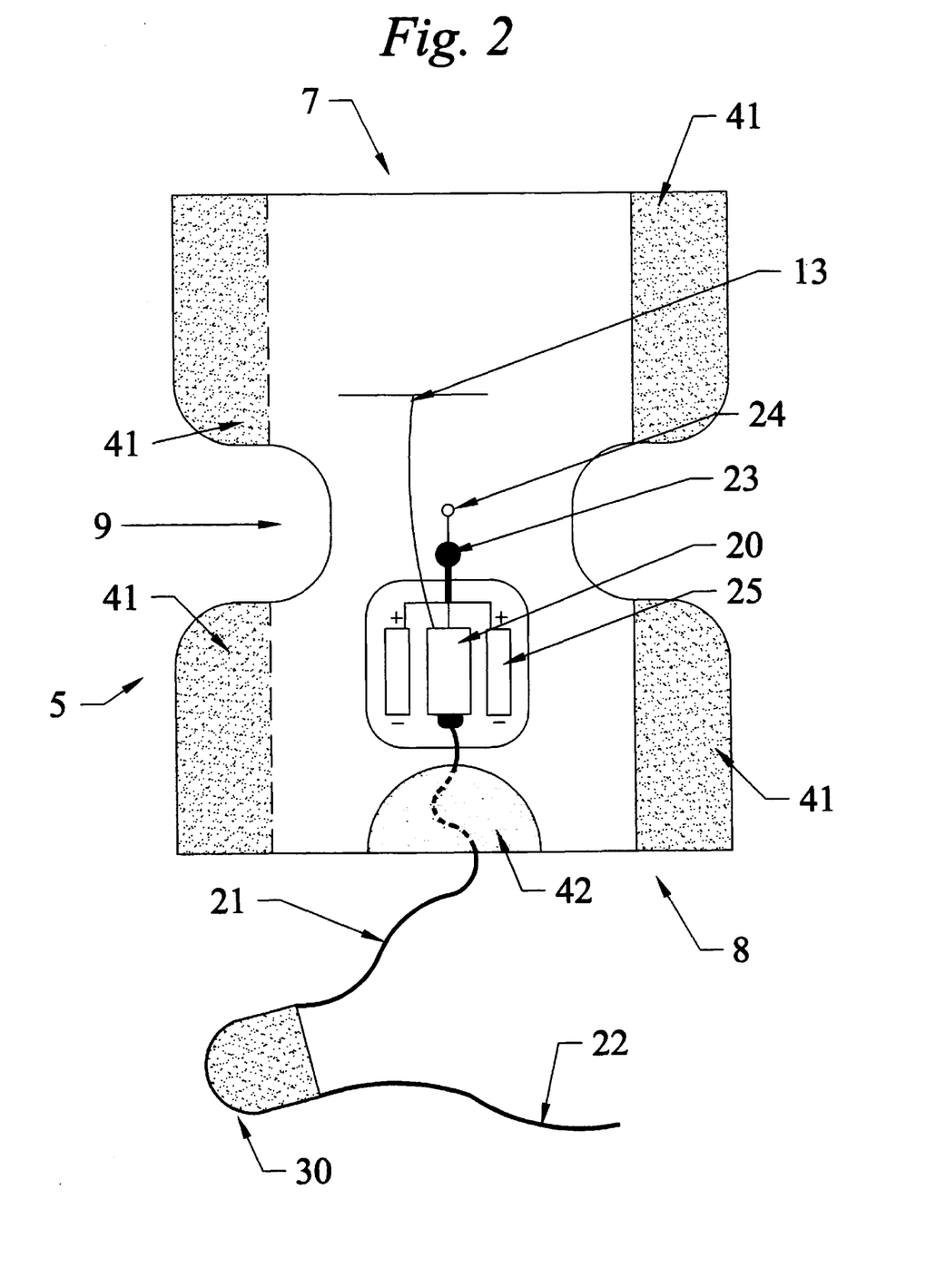
FIG. 2 shows the foot sensing unit of the current invention unfolded and as seen from above.

FIG. 2 shows the foot sensing unit (5) of the blood oxygen monitor and SIDS warning device (1) but in FIG. 2 the foot sensing unit (5) is unwrapped from the foot of an infant, laid out flat, and seen from above. The ankle wrap portion (7) is at the top of FIG. 2. At opposing ends of the ankle wrap portion (7) are miniature hook-and-eye connecting means (41) commonly known by the trade name VELCRO™. The hook portions, from the viewer's perspective, is at the right end of the ankle wrap portion (7) while the eye portion would be underneath and out of sight from a view from above on the left side of the ankle wrap portion (7). However, here it is shown as a series of small dots. Ordinarily, foot sensing unit (5) will be made at least in part of a breathable, somewhat elastic, material not unlike the material used in wrap bandages used for ankle support. The fit of the foot sensing unit (5) is very important for the overall functioning of the unit. It should fit securely and snugly around the ankle of an infant so that it will not be dislodged by the kicking movement common in small infants. To this end, an elastic woven material provides for a snug fit, but not so snug as to affect blood circulation to the foot. The elastic material also provides some degree of adjustability. Adjustability is also provided by the hook-and-eye connecting means (41). These pieces need not mate exactly in order to provide secure attachment of the ankle wrap portion (7) around the ankle of the infant. The arch wrap portion (8) functions similarly. Again, at least a portion of the arch wrap portion (8) will be made of stretchable woven material for a comfortable but secure fit. Again, the hook-and-eye connecting means (41) at the ends of the wings of the arch wrap portion (8) need not mate exactly to provide a secure and tight fit. The transmitting unit (20) is seen centered between the two hook-and-eye connecting means (41) on the arch wrap portion (8). Flanking the transmitting unit (20) are two batteries shown as the power source (25). These batteries provide the power for the transmitting unit (20) as well as the pulse oximeter in the toe cap pulse oximeter (30). A warning light (23) advises the user in the event the batteries are becoming dangerously low on power. A charging inlet (24) is shown in proximity to the power source (25). Extending from the transmitter (20) in a direction opposite from the toe cap pulse oximeter (30) is a small wire antenna (13), which would ordinarily lie across the connector portion (9) and extend up and into the ankle wrap portion (7). A very thin flexible wire antenna may be woven within the materials of the connector portion (9) and the ankle wrap portion (7) without compromising either the elasticity or the comfort of the fit of the foot sensing unit (5). A variety of types of batteries as a power source (25) might be employed. Two 9-volt mercury batteries are a common power source for a pulse oximeter and are sufficient to provide at least 8 hours of continuous operation for many pulse oximeter models. However, rechargeable nickel cadmium batteries are the preferred power source (25), but lithium batteries could also be used. The power source must provide enough power for a continuous operation of both the pulse oximeter in the toe cap (30) and the transmitter (20) for the period of time that the device would be in place. This would ordinarily constitute a normal sleep period for an infant, which would be 8 to 12 hours. The SIDS warning device (1) would not be employed continuously, because parents would have the infant under immediate observation in their presence for much of the day. When the SIDS warning device (1) is not in use, the power source (25) could be recharged or replaced as needed.

The toe cap pulse oximeter (30) is connected to the arch wrap portion (8) by the connecting wires (21) and the elastic connecting cord (22). At the bottom of the arch wrap portion (8), between the transmitting unit (20) and the toe cap pulse oximeter (30), there is a securing flap (42). This allows the connecting wires (21) to have a large degree of slack. This is shown in the approximate "S" shaped broken lines underneath the securing flap (42). The portion of the connecting wires (21) that passes underneath the securing flap (42) is equipped with miniature hooks to attach to the miniature eyes found on the securing flap (42). The securing flap (42) also has miniature hooks on one portion of the flap and miniature eyes underneath it on the arch wrap portion (8). The correct length of a connecting wires (21) will be determined by trial and error. Any slack in the connecting wires (21) will be coiled beneath the securing flap (42), which will be pressed into place so that the miniature hooks-and-eyes will hold the slack of the connecting wires (21) in place, maintaining a constant distance between the toe cap pulse oximeter (30) and the arch wrap portion (8). In a similar fashion the elastic connecting piece (22) will be secured between the two connecting means (41) of the arch wrap portion (8). As with the connecting wires (21) a portion of the end of connecting piece (22) will have miniature hooks for more secure attachment to the connecting means (41). In FIG. 2 the elastic connecting piece (22) is not secured in place because the connecting means (41) of the arch wrap (8) are not connected. However, the connecting wires (21) and the elastic connecting piece (22) will securely and snugly hold the toe cap pulse oximeter (30) in place over the toe of an infant. Additionally, the toe cap pulse oximeter (30) is itself constructed of an elastic woven material. This serves to hold the light emitting unit (35) and the light sensing unit (40) in place opposite of each other as is required for proper functioning of the device. The combination of the elastic material in the toe cap pulse oximeter (30), the adjustable connection of the connecting wires (21), and the elastic connecting piece (22) provide for a snug and secure fit of the toe cap pulse oximeter (30) over the toe of an infant. Moreover, once the appropriate distances are determined and the securing flap (42) is in place, it will ordinarily not require further adjustment to obtain the same snug, repeatable fit. Because the ankle wrap portion (7) and the arch wrap portion (8) are themselves snugly and securely wrapped into place around the foot of an infant, the entire device fits securely but without interfering with the circulation of the foot or the circulation to the great toe of the infant. This secure, repeatable fit is important for avoiding artifactual blood oxygen reading, which can be generated by slippage or other motions while the device is in operation and while the infant is active and moving.

Figure 3:
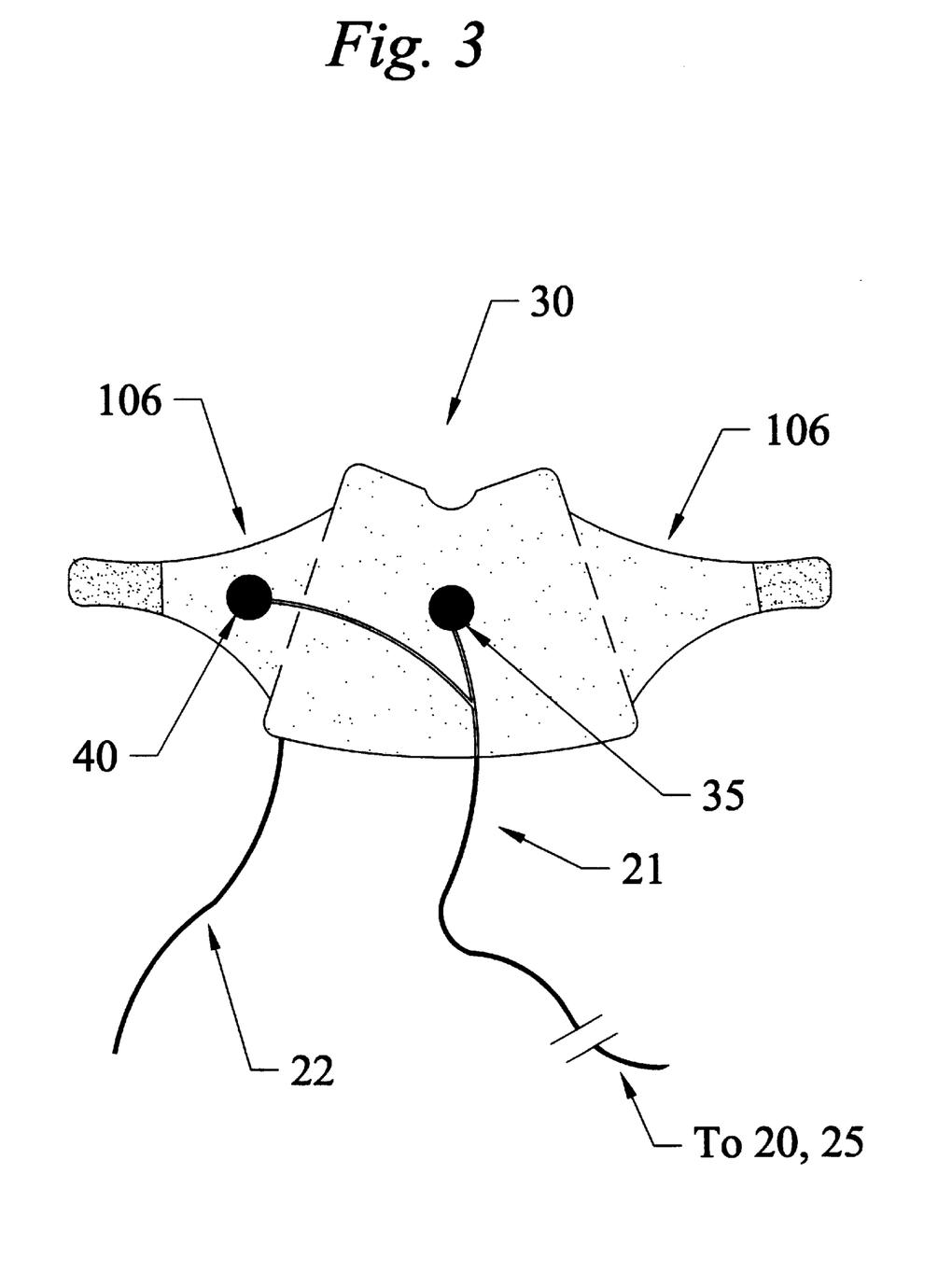
FIG. 3 shows the toe cap pulse oximeter portion of the foot sensing unit in more detail.

FIG. 3 shows in more detail the construction of the toe cap pulse oximeter (30). The toe cap pulse oximeter (30) will consist of a flat piece of elastic material with the light emitting unit (35) and the light sensing unit (40) in a spaced relationship from each other in the elastic material. The connecting wires (21) are ordinarily connected directly to the transmitting unit (20) and the power unit (25) which are not shown in FIG. 3. The elastic connecting piece (22) is ordinarily adjustably connected to the hook-and-eye connecting means (41) of the arch wrap portion (8) of the foot sensing unit (5) (not shown in FIG. 3). On each side of the toe cap pulse oximeter (30) are connecting flaps (106) which are equipped with respectively miniature hooks and miniature eyes. These connecting flaps are also constructed of an elastic material. The toe cap will be folded over over the infant's great toe with the light emitting unit and the light sensing unit positioned on opposite sides of the toe so that light emitted by the light emitting unit (35) will be received and sensed by the light sensing unit (40) after passing through the great toe of the infant. Once this position is achieved, the connecting flaps (106) are folded over and wrapped against each other so that miniature hooks-and-eyes will engage and hold the toe cap in place.

Figure 4:
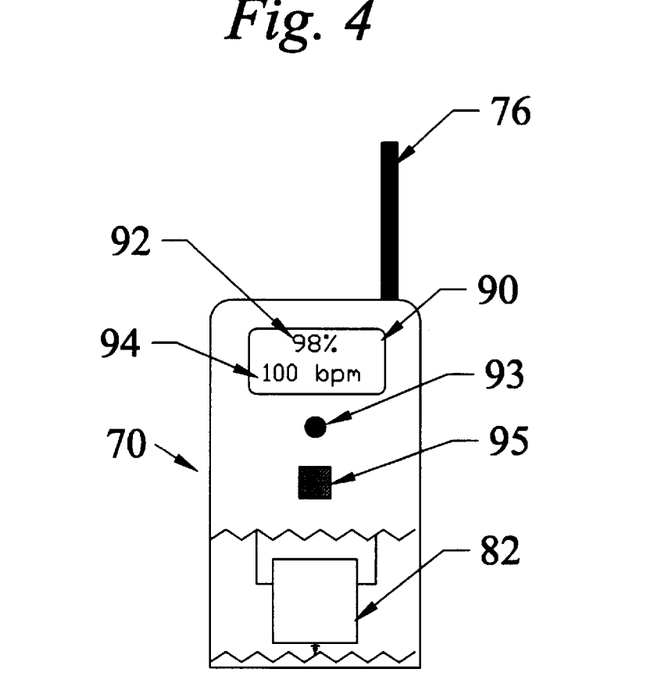
FIG. 4 and FIG. 4A shows the monitoring unit with different portions shown in cut-a-way.
Figure 4A:
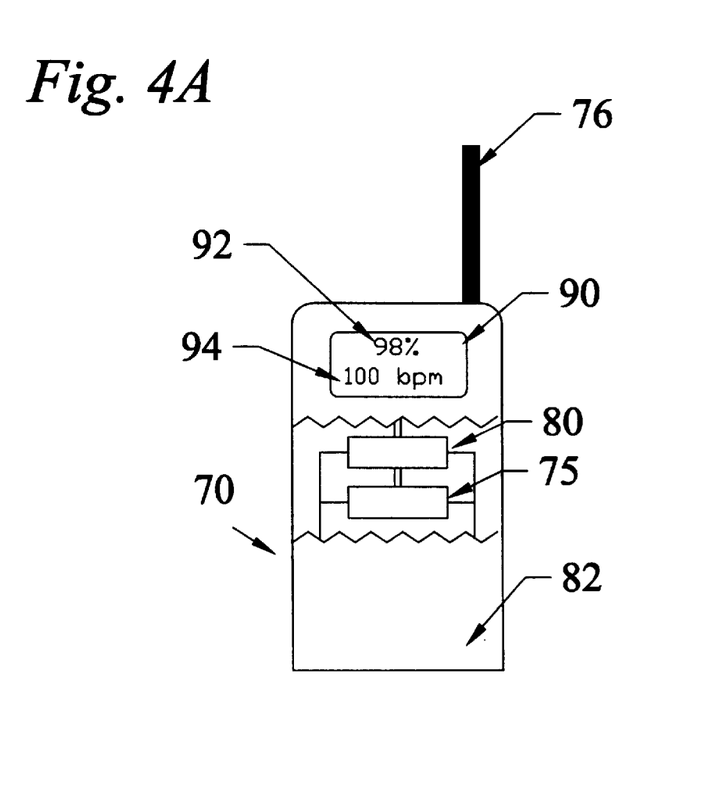

FIG. 4 and FIG. 4A shows the monitoring unit (70). In FIG. 4 a portion of the monitoring unit (70) is cut-a-way for better visualization of the monitoring power source (82). The monitoring unit (70) is approximately the size of a cell phone receiver. Like a cell phone it will have a truncated antenna (76). The monitor power source (82) will ordinarily be a battery. Different batteries may function best for different applications but, ordinarily, a rechargeable nickel cadmium battery is preferred. As with a cell phone receiver or portable phone, the monitoring unit (70) may be connected directly to house current by means of a base recharging unit (100) (shown in FIG. 9). The base recharging unit (100) could serve to both recharge the monitor power source (82) and for operation of the monitoring unit (70) by household current where portable operation is not required. There is a sound generator (95) on the front of the device. This gives an audible warning in the event an unacceptable low blood oxygen reading is recorded. A battery warning light (93) advises the operator of the unit in the event that the battery is becoming discharged. This helps prevent malfunction of the device due to low battery power. At the top is a readout (90). This displays a blood oxygen saturation reading (92) and a pulse rate (94). These are shown with typical values of 98% for the blood oxygen saturation reading (92) and 100 for the pulse rate (94). This display will ordinarily be the standard liquid crystal display visible in most lighting conditions. FIG. 4A shows the middle portion of the monitoring unit (70) cut-away. The monitoring power supply (82) (not shown) is connected to the controller unit (80) and to the receiver unit (75). The receiver unit (75) receives radio signals from the transmitting unit (20) in the foot sensing unit (5) (not shown). The receiving unit (75) translates the radio signals into an analog signal to the controller unit (80). The controller unit (80) has computer chips and logic circuitry required to translate the analog signal into a digital readout (90) showing both the blood oxygen saturation (92) and the pulse rate (94). The logic circuitry will activate the sound generator (95) in the event the logic circuit determines that the blood oxygen saturation (92) is too low for safety. The controller unit (80) can also sense when the monitoring power source (82) is low on power and activate the battery warning light (93).

Figure 5:
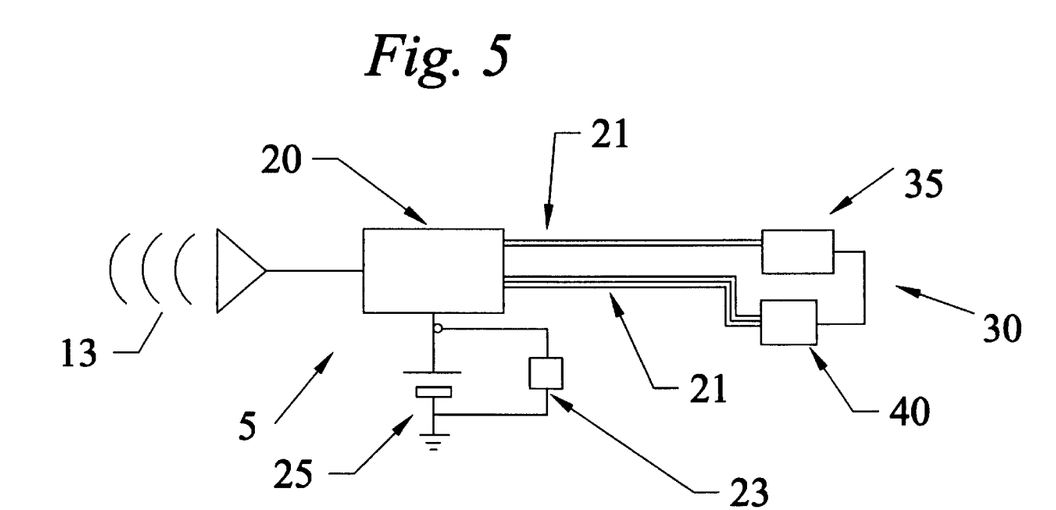
FIG. 5 shows a diagram of the foot sensing unit.

FIG. 5 shows in diagram form the foot sensing unit (5). The transmitting unit (20) is connected to the power supply (25) and to an antenna (13). The power supply (25) is wired through the transmitting unit (20), through the connecting wires (21), to the toe cap pulse oximeter (30). The light emitting unit (35) and the light sensing unit (40) are shown. A total of five different electrical connections connect the toe cap pulse oximeter (30) to the transmitting unit (20). Two of the electrical connections in the electrical connecting wires (21) take power to the light emitting unit (35). Two more electrical connections take power to the light sensing unit (40). One wire transmits the signals generated by the light sensing unit (40) to the transmitting unit (20). The transmitting unit (20), by means of the antenna (13), broadcasts a radio signal shown as wavy lines emitting from the antenna (13) to the monitoring unit (70) (shown in FIG. 6). Also shown is a low-voltage sensor warning light (23). This advises the operator of the unit in the event the battery power is low. As an additional safeguard, in the event the transmitting unit (20) stops operating, the monitoring unit (70) will sound an alarm. Thus, if for some reason the power supply (25) dies immediately or there is a short in the electrical circuit, even though the low-voltage warning light (23) may remain unlit, the monitoring unit (70) will still sound an alarm.

Figure 6:
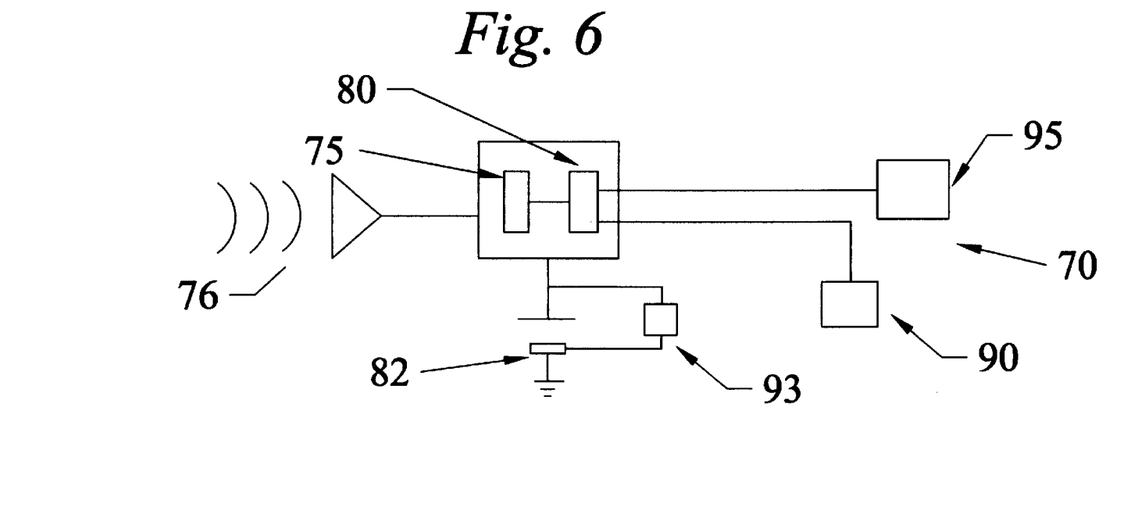
FIG. 6 shows a diagram of the monitoring unit.

FIG. 6 shows the monitoring unit (70) in diagram form. There is an antenna (76) shown receiving radio waves generated by the foot sensing unit (5) (shown in FIG. 5). These signals are transmitted to the receiving unit (75) which converts them into a signal sent to the controller unit (80). It is connected to the monitoring power supply (82). Also connected to the monitoring power supply (82) is the low battery warning light (93). The controller unit (80) generates a signal to the digital readout (90) to generate $O_2$ and pulse readings. The controller unit (80) also sends signals to the sound generator (95) to sound an alarm if necessary.

Figure 7:
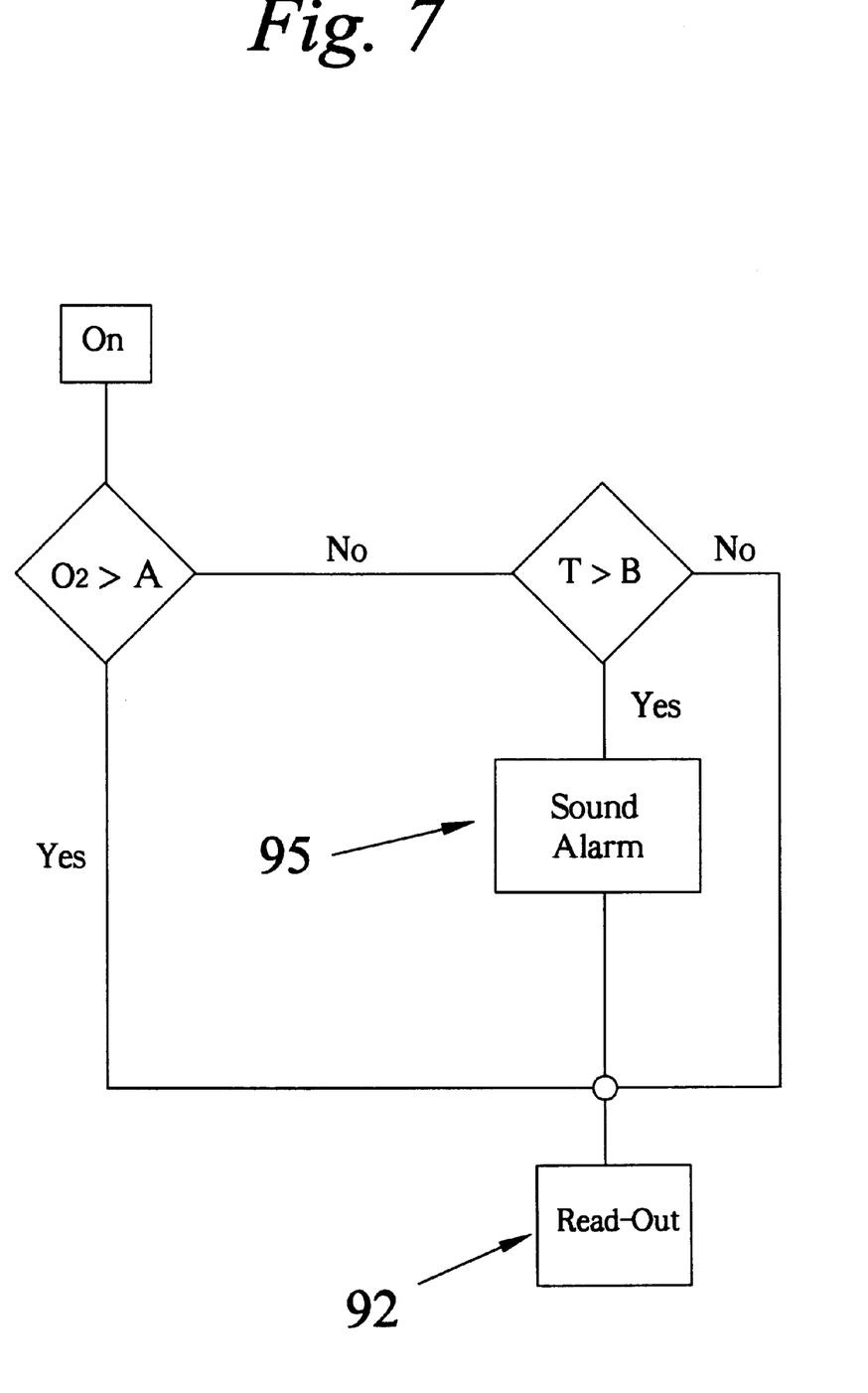
FIG. 7 shows a flow chart for the logic employed by the invention.

FIG. 7 shows, the logic employed by the controller unit (80). Once the device is on there is a continuous check of the oxygen readout. If the oxygen saturation $O_2$ is greater than a predetermined value A, then a signal is transmitted to the blood oxygen saturation readout (92) to show the value of $O_2$. If that signal is below the specified value A, then a signal goes to a time determinator. The $O_2$ values are continuously sent from the toe cap pulse oximeter (30) by the transmitter (20). The very first time a continuous reading drops below the predetermined value A, this starts the time clock in the time determinator. As long as the $O_2$ value is below A, the signal continues to feed into the time determinator. At the onset of the first low signal, the time clock starts running until a predetermined time B has elapsed. If, during this delay period, the $O_2$ readout increases to where it is greater than the predetermined value A, then the time stops and is reset to O and the readout signal is again forwarded directly to the readout (92). However, as long as the $O_2$ reading remains below A, the signal is diverted to the time determinator. If, during the time B, the $O_2$ goes above A, then no further action is taken. However, if the $O_2$ readout remains below A for the predetermined time B, then the alarm (95) sounds alerting the operator that the $O_2$ level has remained below the predetermined set value A for the predetermined set time B.

The purpose of insuring there is a time delay between the first low $O_2$ reading and the sounding of an alarm is to avoid alarms caused by temporarily low readings, which may be caused by motion of the infant, unusual positions, or even transient physical events like sneezing or coughing. Ordinarily, these predetermined values A and B will be set at the factory and cannot be changed by the operator. If the sound alarm (95) goes off, it alerts the parents that their baby must be immediately checked to determine the cause of the low oxygen readings. If there is nothing apparently wrong with the baby and it appears to be normal, the parent may turn off the monitoring unit (70), which resets the logic circuitry and stops the alarm (95). The monitoring unit will be turned on which starts the reception of oxygen readings again. If continuous low oxygen readings continue to be received, the alarm will sound again. In this case the parent may wish to check the foot sensing unit to be sure it is still in position and that it is operating properly. If no signal is being received from the foot sensing unit, this will automatically cause the alarm to go off, because no signal will be read by the logic circuitry as a $O_2$ reading of O. Ordinarily, if the device is functioning properly, the batteries are operating properly, then no more than a readjustment of the foot sensing unit should be required for the operation to resume normal readings and for the alarm to stop sounding. If the alarm continues to sound after these precautionary measures are taken, it may be necessary to awaken the baby or to take other steps to be sure the low oxygen readings are artifactual, rather than a reflection of a serious respiratory distress on the part of the infant being monitored.

Figure 8:
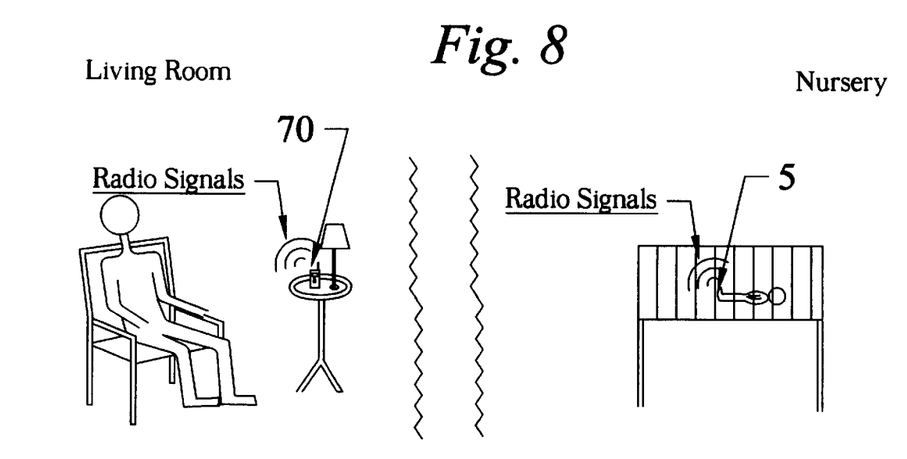
FIG. 8 shows the current invention in use.

FIG. 8 shows the SIDS Warning Device (1) in use. The monitoring unit (70) is shown on a table by a chair having a parent or other caregiver in a living room. The foot sensing unit (5) is in place on a baby lying in a crib in a nursery. Wavy lines labeled radio signals are generated by the foot sensing unit (5) in place on the baby in the nursery and are received by the monitoring unit (70) in the living room where the caregiver is located. There is a continuous readout on the monitoring unit (70) of the blood oxygen saturation level and of the pulse rate for the baby to whom the foot sensing unit (5) is affixed.

Figure 9:
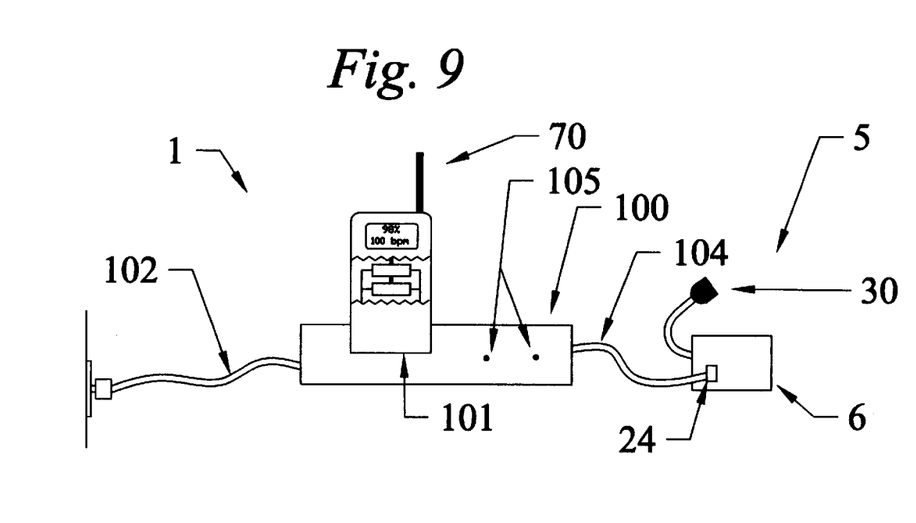
FIG. 9 shows the current invention being recharged.

FIG. 9 shows the entire SIDS warning device (1) in place. The monitoring unit (70) is inserted into a recharging unit (100) which is connected to wall current by a standard electrical connecting cord (102). At the base of the monitoring unit (70) will be connections (101) for recharging the monitor power source (82) by current received from the wall plug (102) and passing through an appropriate transformer in the recharging unit (100). Likewise, there is a recharging cord (104) which connects to charging inlet (24) on the foot sensing unit (5). The toe cap pulse oximeter (30) is not in use and the wrap unit (6) is folded up and placed in a convenient location next to the recharging unit (100). Ordinarily, when the SIDS warning device (1) is not in use, it will be placed in position as is shown in FIG. 9 for recharging. There are indicator lights (105) on the recharging unit (100) to indicate when both the monitoring unit (70) and the foot sensing unit (5) are recharging. Once they are fully charged, the light will go out. When the child is awake and active, there is no reason for the SIDS warning device (1) to be in place or functioning. It will be both stored and recharged at its location on the recharging unit (100). Only when the baby is to be placed in bed or otherwise is in a position where there is vulnerability to a SIDS event will the foot wrap unit (5) be placed around the infant's foot and the monitoring unit (70) activated so that the caregiver can give appropriate monitoring of the infant's condition.

I claim:

1. A portable adjustable cordless device to alert caregivers of the onset of Sudden Infant Death Syndrome occurring in an infant comprising:

(a) an extremity mounted apparatus wherein:
said apparatus has means for adjustably fitting around an extremity of the infant;
said apparatus has self-contained means for determining blood oxygen levels;
said apparatus has self-contained cordless means for transmitting said blood oxygen levels determined by said self-contained means for determining blood oxygen;
said apparatus has first means for powering said self-contained determining means and said self-contained transmitting means and;
said apparatus is constructed of a first portion that is, at least in part, made of stretchy elasticized material and of a second portion designed to fit over the toe of the infant, said second portion equipped with said self-contained means for determining blood oxygen levels in the infant;

(b) a monitor to be kept with a caregiver wherein:
said monitor has means for receiving transmissions of blood oxygen determinations from said cordless transmission means in said apparatus, said blood oxygen determination being made by said self-contained determining means in said apparatus;
said monitor has means for processing blood oxygen determinations,
said monitor has means for sounding an audible alarm if blood oxygen determinations fall below a predetermined level and;
said monitor has a second means for powering said receiving means, said processing means, and said sounding means;

whereby a caregiver may fit said extremity mounted apparatus to an extremity of an infant, placing an infant so fitted with said extremity mounted apparatus into a bed or other resting position, then leaving infant unattended, but keeping said monitor with a caregiver so that a caregiver may listen for said audible alarm and so be alerted to the onset of a Sudden Infant Death Syndrome event.

2. A portable adjustable cordless device of claim 1, wherein said second portion is constructed, at least in part, of stretchy elasticized material so that a tight, but non-binding, fit of said second portion over the toe of an infant is assured.

3. A portable adjustable cordless device of claim 2, wherein said self-contained means for determining blood oxygen levels in said extremity mounted apparatus is a pulse oximeter.

4. A portable adjustable cordless device of claim 3, wherein said second portion is designed as a toe cap to fit over the toe of an infant, said toe cap constructed in a roughly rectangular shape sized for the toe of an infant wherein, at least, part of said toe cap is equipped with miniature hook-and-eye means for attachment and detachment so that said toe cap will adjustably fit around a toe of an infant and snugly enclose a toe of an infant by means of said miniature hook-and-eye attachment means and by said stretchy elasticized material.

5. A portable adjustable cordless device of claim 4, wherein said toe cap is connected to said first portion by adjustable cords adapted for further securing said toe cap to a toe of an infant in a tight, but non-binding, fit whereby motion artifacts causing false alarms are reduced.

6. A portable adjustable cordless device of claim 5, wherein said adjustable cords are constructed, at least in part, with miniature hooks-and-eyes for connection to corresponding miniature hooks-and-eyes on said first portion.

7. A portable adjustable cordless device of claim 6, wherein said first means for powering and said second means for powering are batteries.

8. A portable adjustable cordless device of claim 7, wherein said monitor has a means for displaying pulse readings generated by said pulse oximeter.

9. A portable adjustable cordless device of claim 8, wherein said batteries are rechargeable.

10. A portable adjustable cordless device of claim 9, wherein said portable adjustable cordless device further comprises a base to hold said extremity mounted apparatus and to hold said monitor when not in use, said base connectable to a wall electrical outlet by standard cord and prong connections, said base further containing means for recharging said rechargeable batteries in said extremity mounted apparatus and in said monitor.

11. A portable adjustable cordless device of claim 5, wherein said self-contained cordless means for transmitting blood oxygen levels is a low-powered radio transmitter and said means for receiving transmissions made by said cordless transmission means is a radio receiver.

12. A portable adjustable cordless device of claim 11, wherein said means for processing said blood oxygen determinations has a means for producing a visible readout of said blood oxygen determinations.

13. A portable adjustable cordless device of claim 12, wherein said means for sounding an audible alarm has a means for determining if a blood oxygen determination falls below a predetermined level for a predetermined time before said means for sounding an audible alarm is activated.

14. A portable adjustable cordless device to alert caregivers of the onset of Sudden Infant Death Syndrome occurring in an infant comprising:

a pulse oximeter mounted in an adjustable elastic toe cap;

an adjustable elastic foot wrap adapted for fitting around an ankle and an arch of a foot, said foot wrap housing a low powered radio transmitter and a first set of rechargeable batteries;

adjustable conductive wiring for said pulse oximeter, said batteries and said radio transmitter whereby pulse reading and blood oxygen reading obtained by said pulse oximeter are transmitted by said radio transmitter;

a monitoring unit housing a radio receiver, a controller unit, a readout, a sound alarm, and a second set of rechargeable batteries for powering said receiver, said controller unit, said readout and said sound alarm whereby said receiver receives pulse reading and blood oxygen readings transmitted by said radio transmitter, said controller sends said pulse readings and said blood oxygen readings to said readout and sounds said sound alarm if said blood oxygen readings are below a predetermined amount.

15. A portable adjustable cordless device of claim 14, wherein said portable adjustable cordless device further includes means for timing so that when said monitor receives a continuous blood oxygen reading below said predetermined amount said monitor will not sound said sound alarm until a predetermined amount of time has passed.

16. A portable adjustable cordless device of claim 15, wherein said first set of rechargeable batteries and said second set of rechargeable batteries includes means for detachably connecting to a base recharging unit for recharging when said portable adjustable cordless device is not in use.

17. A portable adjustable cordless device of claim 16, wherein there is a first means for warning a caregiver when said first set of rechargeable batteries is becoming depleted and a second means for warning a caregiver when said second set of rechargeable batteries is becoming depleted.

18. A portable adjustable cordless device of claim 17, wherein said adjustable elastic footwrap is made of a woven, stretchable, breathable material and said adjustable elastic toe cap is made of a woven, stretchable, breathable material.

* * * * *